United States Patent
Bergman et al.

(10) Patent No.: US 10,161,914 B2
(45) Date of Patent: Dec. 25, 2018

(54) INSPECTION METHODS WITH PROBE FOR SUBSTANTIALLY ROUND HOLE

(71) Applicant: General Electric Company, Schenectady, NY (US)

(72) Inventors: Robert William Bergman, Scotia, NY (US); Thomas James Batzinger, Burnt Hills, NY (US); Thomas Earnest Moldenhauer, Burnt Hills, NY (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 78 days.

(21) Appl. No.: 15/385,210

(22) Filed: Dec. 20, 2016

(65) Prior Publication Data

US 2018/0172643 A1  Jun. 21, 2018

(51) Int. Cl.
*G01N 29/26* (2006.01)
*G01N 27/90* (2006.01)
(Continued)

(52) U.S. Cl.
CPC ......... *G01N 29/226* (2013.01); *G01N 27/902* (2013.01); *G01N 27/904* (2013.01); *G01N 27/9086* (2013.01); *G01N 29/262* (2013.01); *G01N 29/265* (2013.01); *G01N 29/30* (2013.01); *G01N 27/9053* (2013.01); *G01N 2291/0234* (2013.01); *G01N 2291/0289* (2013.01); *G01N 2291/106* (2013.01); *G01N 2291/2636* (2013.01)

(58) Field of Classification Search
CPC .. G01D 11/30; G01N 27/9006; G01N 29/043; G01N 29/225; G01N 2291/2636; G01M 15/54

USPC ........................................................... 73/641
See application file for complete search history.

(56) References Cited

U.S. PATENT DOCUMENTS 4,414,508 A  11/1983  Davis et al.
4,425,545 A  1/1984   Scalese
(Continued)

FOREIGN PATENT DOCUMENTS

DE  20 2009 003 635 U1  6/2009
EP     3 199 944 A1      8/2017

OTHER PUBLICATIONS

Extended European Search Report and Opinion issued in connection with corresponding EP Application No. 17205003.1 dated Apr. 23, 2018.

*Primary Examiner* — J M Saint Surin
(74) *Attorney, Agent, or Firm* — Ernest G. Cusick; Hoffman Warnick LLC (57) ABSTRACT

Various aspects include methods of inspecting a substantially round hole in a material. One method can include: feeding a probe axially into the substantially round hole until the probe completely passes through the substantially round hole while the probe is activated; rotating the probe at least ninety degrees around a primary axis of the substantially round hole after feeding the probe completely through the substantially round hole; removing the probe axially from the substantially round hole after rotating the probe at least ninety degrees while the probe is activated; and compiling at least one of eddy current data or ultrasound data about the hole from the feeding of the probe axially into the substantially round hole and the removing of the probe axially from the substantially round hole.

16 Claims, 13 Drawing Sheets

(51) Int. Cl.
*G01N 29/30* (2006.01)
*G01N 29/265* (2006.01)
*G01N 29/22* (2006.01)

(56) References Cited

U.S. PATENT DOCUMENTS

| | | | |
|---|---|---|---|
| 4,864,239 A | 9/1989 | Casarcia et al. | |
| 5,111,142 A | 5/1992 | Mazzone et al. | |
| 5,136,240 A | 8/1992 | Geier et al. | |
| 5,465,045 A * | 11/1995 | DeRock | G01N 27/902 324/220 |
| 5,834,937 A * | 11/1998 | Burris | G01N 27/9013 324/219 |
| 5,903,147 A | 5/1999 | Granger, Jr. et al. | |
| 6,339,331 B1 | 1/2002 | Ruzzo | |
| 7,093,491 B2 | 8/2006 | Murphy et al. | |
| 7,328,619 B2 * | 2/2008 | Moles | G01N 29/0609 73/598 |
| 7,368,907 B2 | 5/2008 | Raulerson et al. | |
| 7,616,001 B2 * | 11/2009 | Itskovich | G01V 3/24 324/367 |
| 8,179,132 B2 | 5/2012 | Wu et al. | |
| 8,640,531 B2 | 2/2014 | Remillard et al. | |
| 8,723,513 B2 | 5/2014 | Ahn et al. | |
| 9,429,546 B2 * | 8/2016 | Williams | G01N 29/24 |
| 9,518,851 B2 * | 12/2016 | Bergman | G01D 11/30 |
| 9,885,805 B2 * | 2/2018 | Hayman | E21B 47/00 |
| 9,945,817 B2 * | 4/2018 | Pember | G01N 29/0654 |
| 2008/0265878 A1 | 10/2008 | Bousquet et al. | |
| 2012/0191377 A1 * | 7/2012 | Engl | G01N 29/069 702/39 |
| 2013/0019927 A1 | 1/2013 | Zimmerman et al. | |
| 2016/0161300 A1 | 6/2016 | Bergman et al. | |

* cited by examiner

INSPECTION METHODS WITH PROBE FOR SUBSTANTIALLY ROUND HOLE

FIELD OF THE INVENTION

The disclosure relates generally to inspection of components. More particularly, the disclosure relates to methods of inspecting a substantially round hole using an eddy current-based or ultrasound-based probe.

BACKGROUND OF THE INVENTION

Industrial machines such as gas turbines have numerous parts having holes therein that require inspection using eddy currents or ultrasound. For example, a bolt hole in a gas turbine part may require such inspection to identify cracks, etc. One challenge in using eddy current and ultrasonic inspection methods is that they require very precise manipulation of the inspection probe. Performing inspections on inner diameter surfaces of larger diameters (e.g., over 2.5 centimeters) makes probe manipulation very difficult. Another challenge is that a probe that employs a single sensor necessitates very long inspection times due to proper inspection coverage requirements. In addition, a single sensor probe requires complex manipulation to ensure adequate inspection coverage.

BRIEF DESCRIPTION OF THE INVENTION

Various aspects include methods of inspecting a substantially round hole in a material. A first aspect of the disclosure provides a method including: feeding a probe axially into the substantially round hole until the probe completely passes through the substantially round hole while the probe is activated; rotating the probe at least ninety degrees around a primary axis of the substantially round hole after feeding the probe completely through the substantially round hole; removing the probe axially from the substantially round hole after rotating the probe at least ninety degrees while the probe is activated; and compiling at least one of eddy current data or ultrasound data about the hole from the feeding of the probe axially into the substantially round hole and the removing of the probe axially from the substantially round hole.

A second aspect of the disclosure provides a method including: mounting a probe on the material proximate the substantially round hole, the probe including: a flexible sheet shaped and biased to substantially conform with a portion of an interior of the substantially round hole; a plurality of sensors disposed on the flexible sheet, each sensor configured to transmit a non-destructive signal into the material for inspecting the substantially round hole; and a probe mount coupled with the flexible sheet, the probe mount for mounting on the material; activating the probe; rotating the flexible sheet at least three-hundred-and-sixty degrees around a primary axis of the substantially round hole after inserting the flexible sheet into the substantially round hole and activating the probe; removing the flexible sheet from the substantially round hole; and compiling at least one of eddy current data or ultrasound data about the hole from the at least one of eddy current data or ultrasound data gathered during the rotating of the flexible sheet within the substantially round hole.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, the disclosure provides probes for inspection methods for a substantially round hole, e.g., a bolt hole or a borehole in a turbomachine component.

Figure 1:
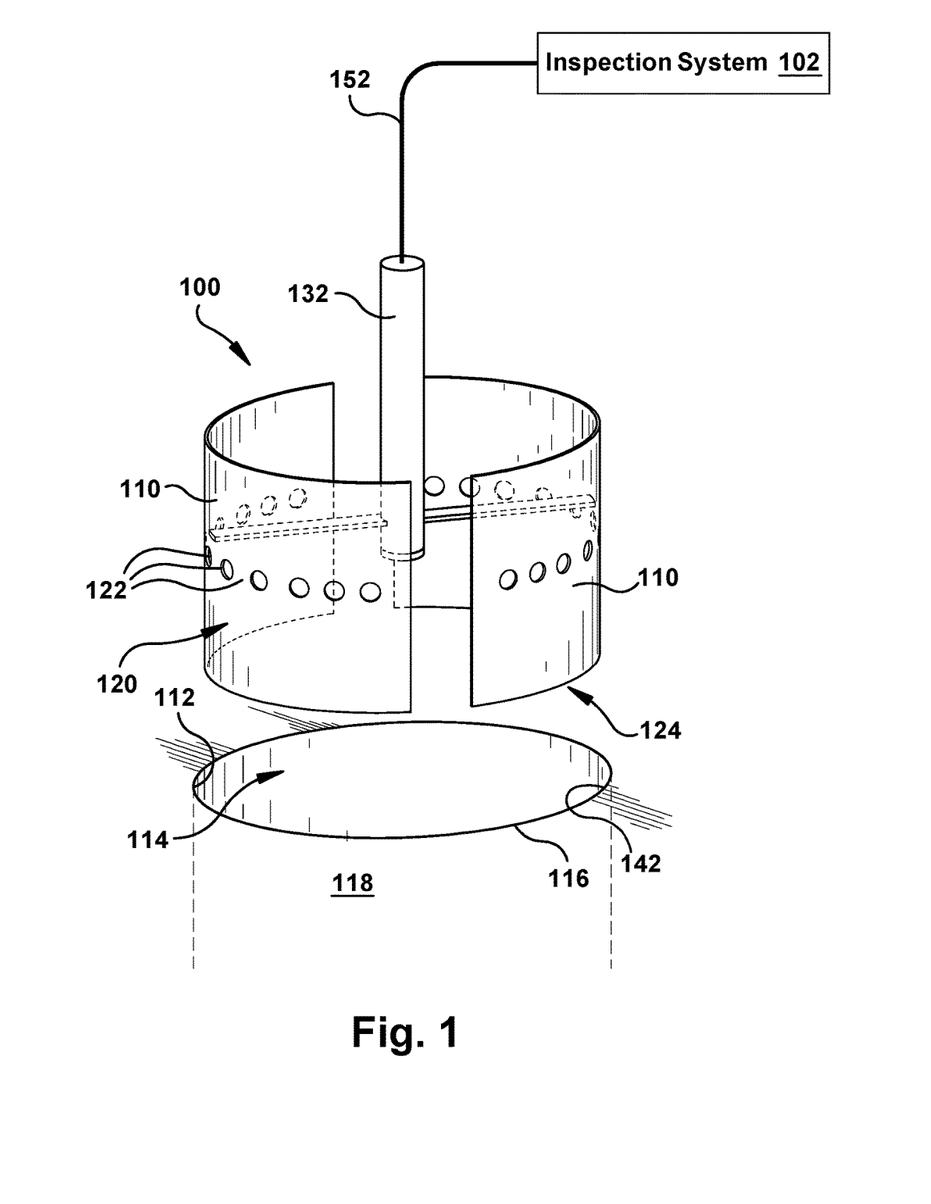
FIG. 1 shows a perspective view of a probe for an inspection system for a substantially round hole according to one aspect of the disclosure.
Figure 2:
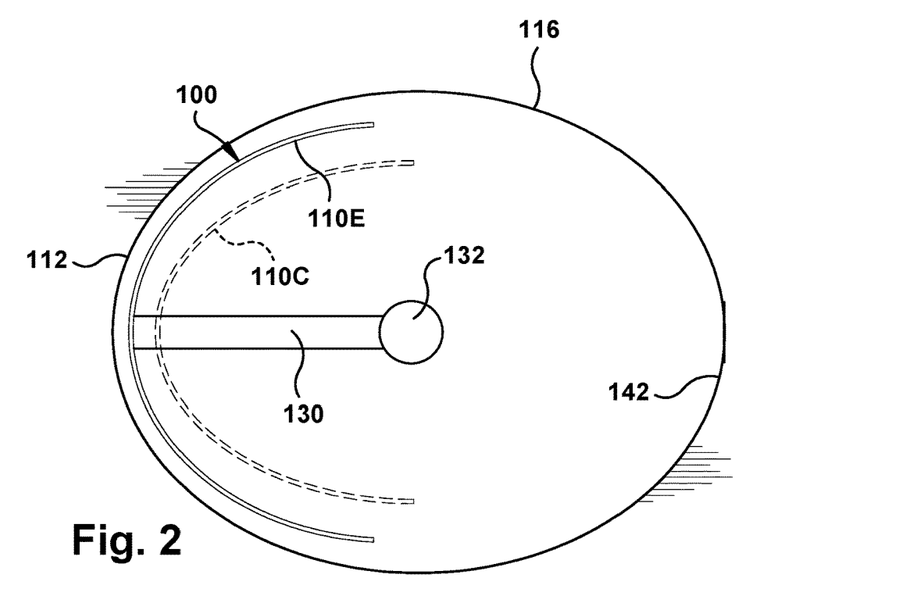
FIG. 2 shows an enlarged plan view of a guide member on the probe of FIG. 1.
Figure 3:
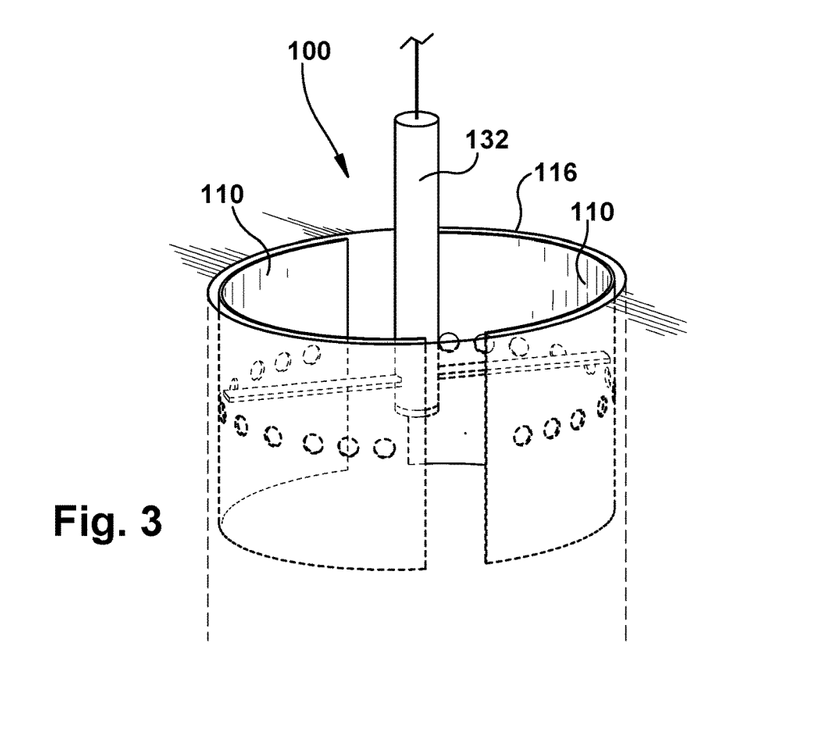
FIG. 3 shows a perspective view of the probe of FIG. 1 in operation.

Referring to FIGS. 1-3, in one embodiment, a probe 100 for an inspection system 102 for a substantially round hole in a material is illustrated. Inspection system 102 may include any now known or later developed eddy current or ultrasound inspection system capable of operatively coupling with a probe according to the invention. As understood, inspection system 102 includes a control system for transmitting either an eddy current or ultrasound signal through a probe, such as probe 100 in FIGS. 1-3 or probe 200 in FIGS. 4-6, receive a return signal and analyze the return signal such that the structure of the material upon which the signals are transmitted can be analyzed and/or imaged. Such inspection systems 102 are capable of, among other things, identifying flaws in the material such as cracks or other imperfections.

As used herein, a "substantially round hole" refers to a hole in a material, e.g., steel, aluminum or other metal or alloy thereof, that has at least a portion that has a rounded, oval, circular or near circular cross-section. In one example, the hole may be a threaded opening such as a bolt hole in a part of a gas turbine. In another example, the hole may be a borehole in a part of a gas turbine (e.g., an unthreaded opening). A large variety of alternative examples will be apparent to one with skill in the art.

Referring to FIG. 1, probe 100 may include a flexible sheet 110 shaped and biased to substantially conform with a portion 112 of an interior 114 of a substantially round hole 116 in a material 118. In one embodiment, flexible sheet 110 may include a polystyrene substrate; however, a variety of other flexible sheet materials may be employed such as but not limited to polytetrafluorethlene (PTFE) and vinyls. A plurality of sensors 122 may be disposed on flexible sheet 110 such that each sensor 122 can transmit a non-destructive signal into material 118 for inspecting the substantially round hole, i.e., by inspection system 102 analyzing a return signal received by sensors 122. In various embodiments, as shown in FIG. 1, a pair of flexible sheets 110 can be positioned symmetrically within hole 116. As noted herein, the non-destructive signal may include one of an eddy current signal and an ultrasound signal. Each sensor 122 may take any appropriate form based on the type of signal used, e.g., any combination of coils for eddy current, or an ultrasound transducer for transmission and reception of ultrasonic signals. In one embodiment, as shown in FIG. 1, plurality of sensors 122 may extend along a line 124 on flexible sheet 110, and along substantially the entire length of each flexible sheet 110. In this manner, as probe 100 enters or exits hole 116, it is evaluating at least half of the hole, e.g., at least 180° of the round hole. While a linear arrangement has been illustrated, other arrangements may be provided depending on the shape of portion 112. For example, two lines of sensors, a sinusoidal line, an array of sensors, etc., may be employed.

Flexible sheet 110 may be initially shaped to substantially conform to portion 112, e.g., by having a particular length and radius of curvature. For example, the polystyrene substrate may have a shape configured to substantially conform to portion 112 of interior 114 of substantially round hole 116. For example, if hole 116 has a diameter of 1.2 centimeters, each flexible sheet 110 may have a radius of curvature of 0.6 cm (radius of hole 116) and a length approximately 1.9 cm (just over half of the circumference of hole 116). In addition, as shown in FIG. 2, each flexible sheet 110 may be flexible between a first, compressed position (110C dashed line in FIG. 2) sized to fit into an end of substantially round hole 116 and a second, expanded position (110E solid line in FIG. 2) sized to substantially conform with portion 112 of interior 114 of substantially round hole 116. In this fashion, probe 100 can be readily inserted into hole 116 without a drastic amount of manipulation in the first, compressed position, and then allowed to expand for use to the second, expanded position. In one example, as shown in FIG. 1, portion 112 may be shaped to engage a substantially semi-circular portion of interior 114 of substantially round hole 116, and each flexible sheet 110 may be sized to substantially conform with the substantially semi-circular portion of the interior of the substantially round hole. Alternatively, as shown in FIG. 2, portion 112 can be more arcuate than substantially semi-circular where hole 116 is not exactly circular.

As shown in FIGS. 1 and 2, probe 100 may also include a probe support 130 (FIG. 2 only) coupled to flexible sheet 110 for supporting the flexible sheet relative to substantially round hole 116. A handle 132 may be coupled to probe support 130 for controlling a position of the probe. Probe support 130 and handle 132 may be made of any material having sufficient strength to manipulate the position of corresponding flexible sheet 110, e.g., a metal or hard plastic. Probe support 130 may be coupled to corresponding flexible sheet 110 in any now known or later developed fashion, e.g., mechanical fasteners such as screw(s), adhesives, etc. Probe support 130 and handle 132 may be coupled in a similar fashion or may be made as a one-piece structure.

As illustrated in FIG. 1, any wiring 152 that may be necessary to couple inspection system 102 to sensors 120 can be placed along or within handle 132 and/or along or within probe support 130. Any now known or later developed transition seals or hardware necessary to protect the wiring relative to openings, e.g., within the handle, or moving parts may be employed.

In operation, as shown in FIGS. 2 and 3, probe 100 will allow for an inspection of a substantially round hole (or simply, hole) 116 by feeding the probe containing sensors 120 into the hole. As probe 100 is directed into hole 116, sensors transmit/receive an appropriate signal into about half of the hole, e.g., approximately 180°, resulting in an inspection of about half the hole. Once probe 100 is fed through in one direction, probe 100 may be rotated approximately 180° and pulled back through the hole resulting in an inspection of the remaining half of the hole. During insertion and retraction, each flexible sheet 110, maintains good conformance with portion 112 of interior 114 of hole 116, providing good quality eddy current or ultrasound data for inspection system 102.

Figure 4:
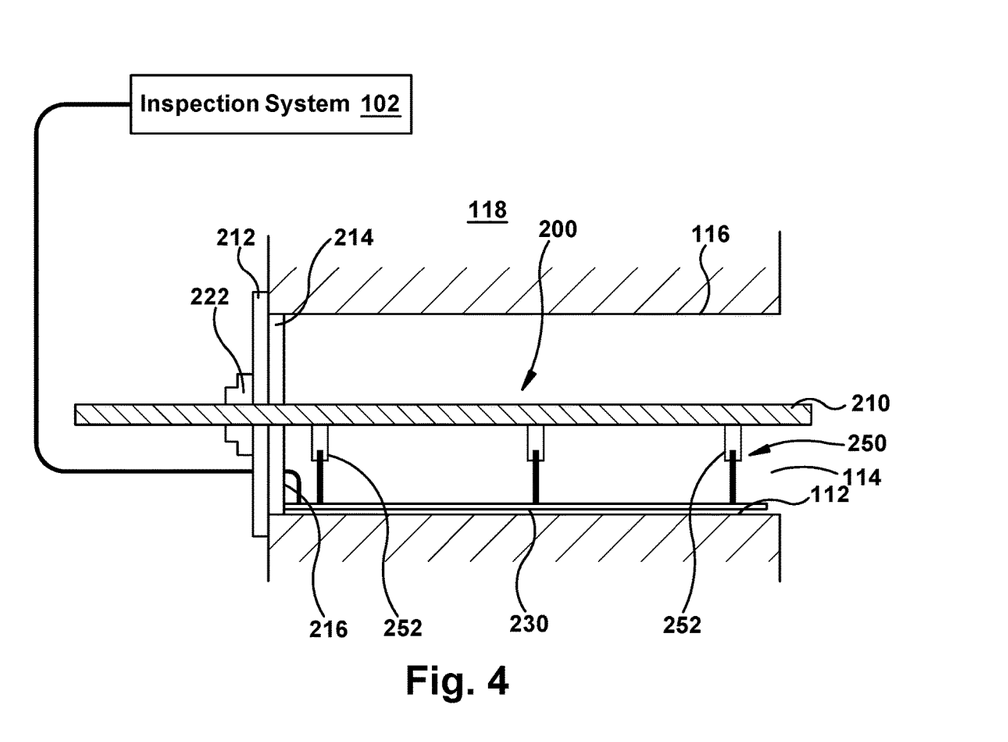
FIG. 4 shows a schematic cross-sectional view of a probe for an inspection system for a substantially round hole according to another aspect of the disclosure.
Figure 5:
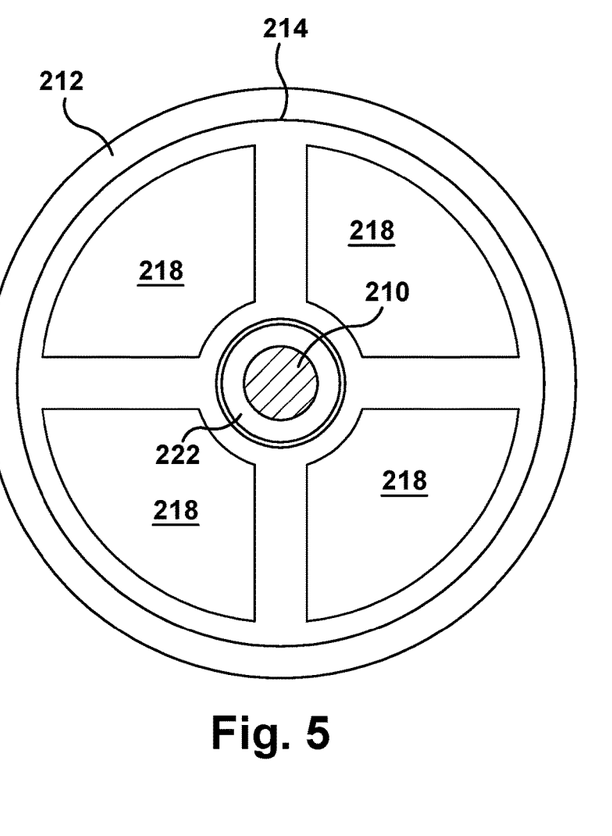
FIG. 5 shows a side view of a bearing plate of the probe of FIG. 1 according to an aspect of the disclosure.
Figure 6:
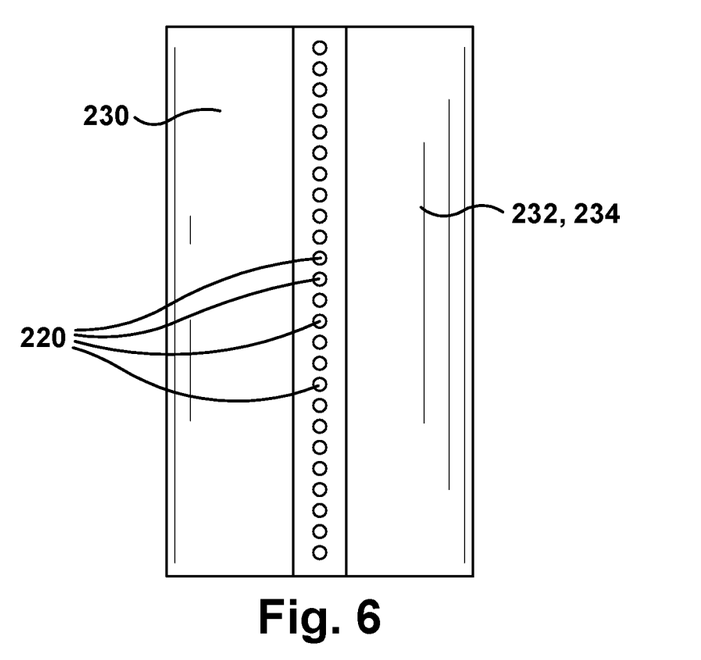
FIG. 6 shows a plan view of a sensor mount surface of the probe of FIG. 4 according to an aspect of the disclosure.

Turning to FIGS. 4-6, another embodiment of a probe 200 for inspection system 102 for substantially round hole 116 in material 118 is illustrated. In this embodiment, probe 200 may include an elongated sensor support 210. Elongated sensor support 210 is elongated sufficiently to ensure full sensor coverage over a length of hole 116, i.e., all relevant parts of hole 116 are capable of being evaluated. A bearing plate 212 is configured to rotatably support elongated sensor support 210 in a position in substantially round hole 116. As illustrated, bearing plate 212 positions elongated sensor support 210 such that it is centered in hole 116; however, this is not necessary in all instances, e.g., for oblong rounded holes. In any event, bearing plate 212 may include a mount surface 214 configured to mate with an end 216 of substantially round hole 116 to position elongated sensor support 210. Mount surface 214 may be shaped to match end 216 such that bearing plate 212 positions sensor support 210 appropriately, and may turn in end 216 where end 216 and support 214 are substantially concentric. As shown in FIG. 5, bearing plate 212 may also include at least one passage 218 therethrough to allow wiring to be coupled to sensors 220 (FIGS. 6 and 7) (where necessary), viewing into hole 116, etc. While four passages are illustrated, any number may be used. While mount surface 214 is illustrated as a substantially circular member in FIG. 5, mount surface 214 need not be continuous as circumferentially space members on bearing plate 212 may be employed.

Elongated sensor support 210 is rotatably coupled to bearing plate 212 by a bearing 222 that may limit rotation of elongated bearing support 210 to just greater than 360° (e.g., 362°, 365°, 370°, etc.), the purpose of which will be described herein. "Just greater than 360°" can be any amount close to 360° that ensures all of hole has been evaluated without a large amount of overlap. Bearing 222 may limit rotation of elongated bearing support 210 in any known fashion, e.g., rotational stops on, in or adjacent bearing 222 and/or on, in or adjacent support 210. In addition, a starting location can be set or keyed with bearing 222 to ensure that all measurements start at the same location. Support 210, bearing plate 212 and bearing 222 may be made of any material having sufficient strength to support sensors 220, e.g., a metal or hard plastic.

Figure 7:
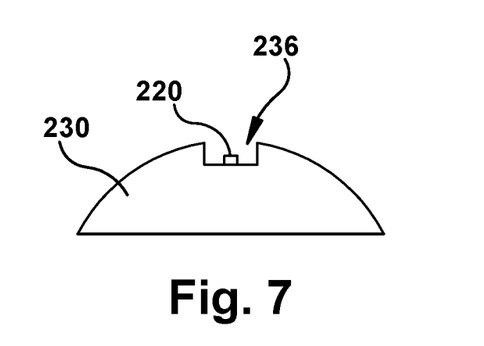
FIG. 7 shows a side view of a sensor mount surface of the probe of FIG. 4 according to an aspect of the disclosure.

FIG. 6 shows a plan view and FIG. 7 shows a side view of a sensor mount surface 230 of probe 200 of FIG. 4 according to an embodiment of the invention. As illustrated, sensor mount surface 230 may be shaped to substantially conform with portion 112 (FIG. 4) of interior 114 (FIG. 4) of substantially round hole 116 (FIG. 4). As noted herein, portion 112 may include a substantially semi-circular portion of interior 114 of substantially round hole 116, and the sensor mount surface is sized to substantially conform with at least some portion of the substantially semi-circular portion of the interior of the substantially round hole. Accordingly, in one embodiment, sensor mount surface 230 may have a fixed curvature to accommodate the smallest hole 116, i.e., portion 112, for which probe 200 (FIG. 4) may be applied. In this case, sensor mount surface 230 may be made of a rigid material 232 such as a metal or hard plastic. In another embodiment, sensor mount surface 214 may include a flexible sheet 234 shaped and biased to substantially conform with portion 112 of interior 114 of substantially round hole 116. Flexible sheet 234 may be of the same material as flexible sheet 110, described herein, e.g., a polystyrene substrate. As with flexible sheet 110, flexible sheet 234 may be flexible between a compressed and expanded state. Flexible sheet 234 along with elongated sensor support 210 each have a length ensure complete measurements of the length of hole 116, and may be changed in length to accommodate different length holes.

As shown in the plan view portion of FIG. 6, a plurality of sensors 220 may be disposed on sensor mount surface 230. Each sensor 220 may be configured to transmit a non-destructive signal into the material for inspecting substantially round hole 116 (FIG. 4). As noted herein, the non-destructive signal may include an eddy current signal or an ultrasound signal. In addition, plurality of sensors 220 may be arranged on sensor mount surface 230 in a wide variety of arrangements to accommodate different holes 116, e.g., parallel lines, sinusoidal, arrays, etc. In the embodiment illustrated, for example, sensors 220 extend along a longitudinal line on sensor mount surface 230, and may extend along substantially an entire length of sensor mount surface 230. In one embodiment, sensor mount surface 230 may include, as shown in the side view of FIG. 7, a channel 236 along a longitudinal axis thereof. Plurality of sensors 220 may be disposed within channel 236 to protect sensors 220 in situations where protection is necessary such as in hole 116 having a rough surface interior.

Returning to FIG. 4, probe 200 may also include a biasing element 250 coupling sensor mount surface 230 and elongated sensor support 210. Biasing element 250 biases sensor mount surface 230 to substantially conform with portion 112 of interior 114 of substantially round hole 116. In the example shown, biasing element 250 includes a plurality of pneumatic rams 252 distributed along a length of sensor mount surface 230. Although three rams 252 are shown, any number may be employed to sufficiently bias sensor mount surface 230. In addition, while pneumatic rams are illustrated, biasing element may employ any form of biasing system now known or later developed such as but not limited to springs, hydraulic rams, etc. The size and/or location of biasing element 250 may be changed to accommodate different sized holes 116. Biasing element 250, e.g., rams 252, may be coupled to sensor support 210 and sensor mount surface 230 using any now known or later developed solution, e.g., mechanical fasteners such as hinges, pivot joints, screws, etc.; welding; adhesives; etc. In addition, while biasing element 250 is illustrated as having rams 252 arranged in a linear fashion relative to sensor mount surface 230, the rams or other biasing elements may be circumferentially displaced along the arc sensor mount surface 230 in order to distribute the bias across the circumference of the surface. Furthermore, although only one ram is shown at each axial location, one or more rams or other biasing elements may be employed at each axial location along support 210.

In operation, as shown in FIG. 4, probe 200 will allow for an inspection of hole 116. Once probe 200 is placed in hole 116, biasing element 250 can be activated, e.g., by applying pneumatic pressure to rams 252, to ensure sensor mount surface 234 adequately contacts or is close enough to portion 112 for sensors 220 to operate. At this point, inspection system 102 can activate sensors 220 and sensor support 210 can be rotated to expose an entirety of hole 116 to sensors 220 through just greater than 360° rotation (e.g., 361°, 364°, 369°, etc.) of sensor support 210. In this fashion, a complete inspection of hole 116 can be completed with biasing element 250 maintaining good conformance with portion 112 of interior 114 of hole 116, providing good quality eddy current or ultrasound data for inspection system 102.

Either of the embodiments provides information may be used to extend the operation life of industrial parts having holes 116 therein, e.g., gas turbine components.

Figure 8:
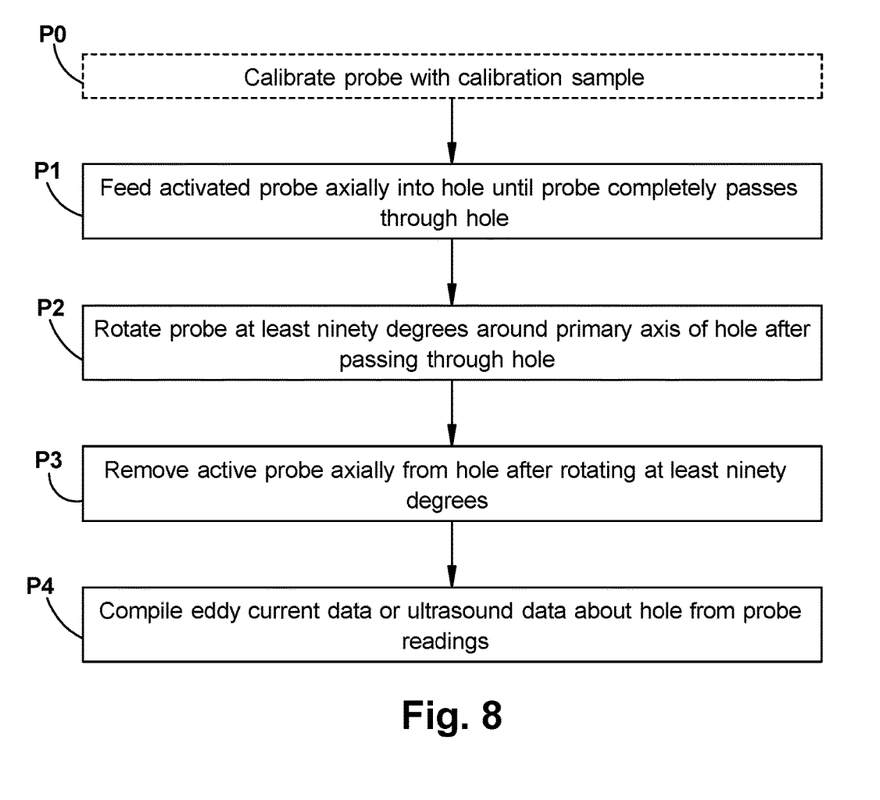
FIG. 8 shows a flow diagram illustrating processes according to various aspects of the disclosure.
Figure 9:
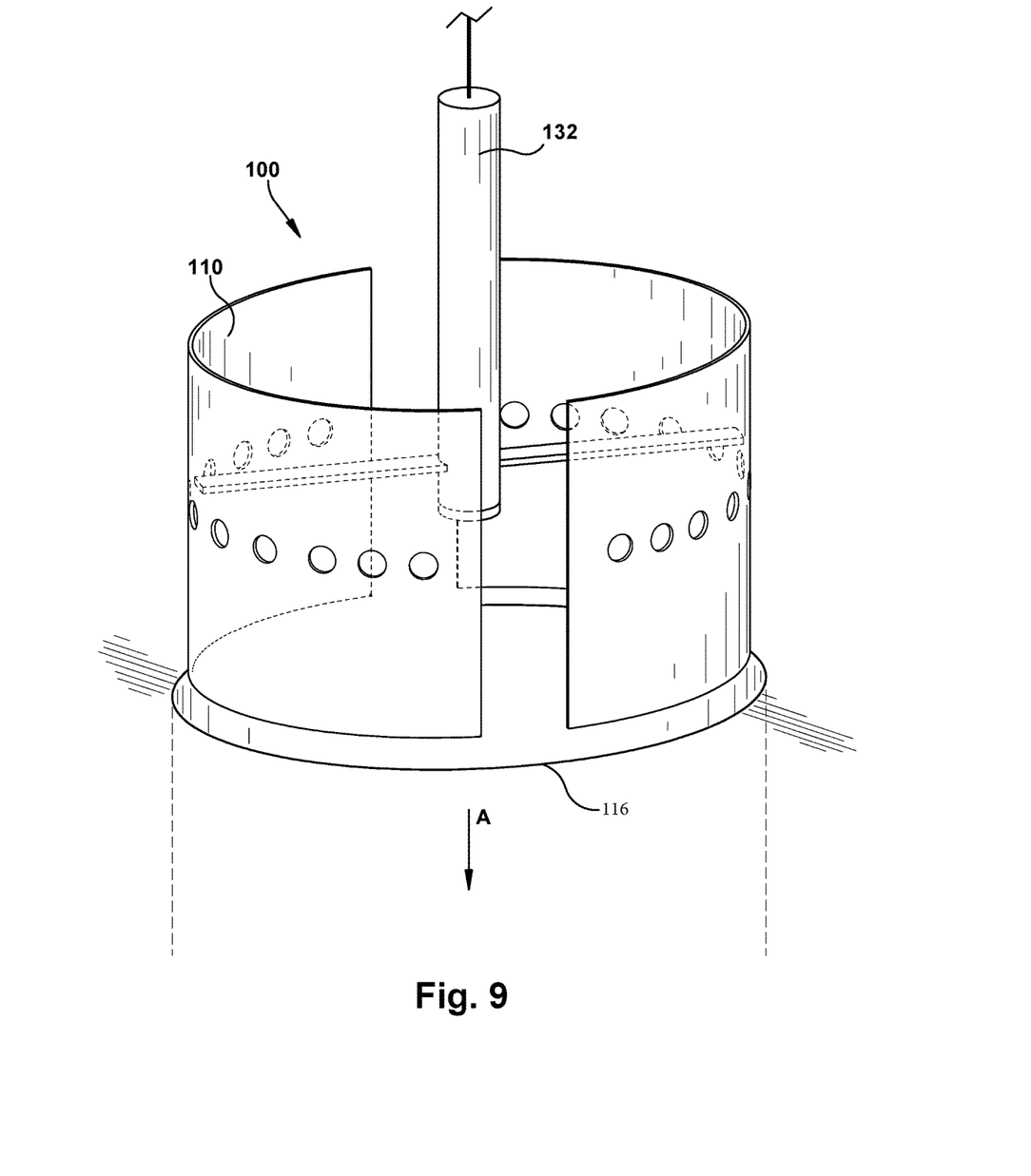
FIGS. 9-12 illustrate perspective views of the probe of FIG. 1 while performing processes according to the flow diagram of FIG. 8.

FIG. 8 shows a flow diagram illustrating processes in a method according to various embodiments of the disclosure. These processes are illustrated along with the schematic depictions of probe 100 in FIGS. 1-3 and the corresponding depictions in FIGS. 9-12. In various embodiments, processes in the flow diagram of FIG. 8 include:

Process P1: feeding probe 100 axially into substantially round hole 116 until probe 100 completely passes through substantially round hole 116 (FIG. 3; FIG. 9), while probe 100 is activated. In some cases, this process can include activating probe 100 via inspection system 102, to transmit non-destructive signals (e.g., eddy current or ultrasound signals), and manually (e.g., by hand, via a tool or other holder engaged with handle 132) feeding probe 100 axially (along primary axis A of substantially round hole 116) into hole 116 until flexible sheet 110 completely enters hole 116.

Figure 10:
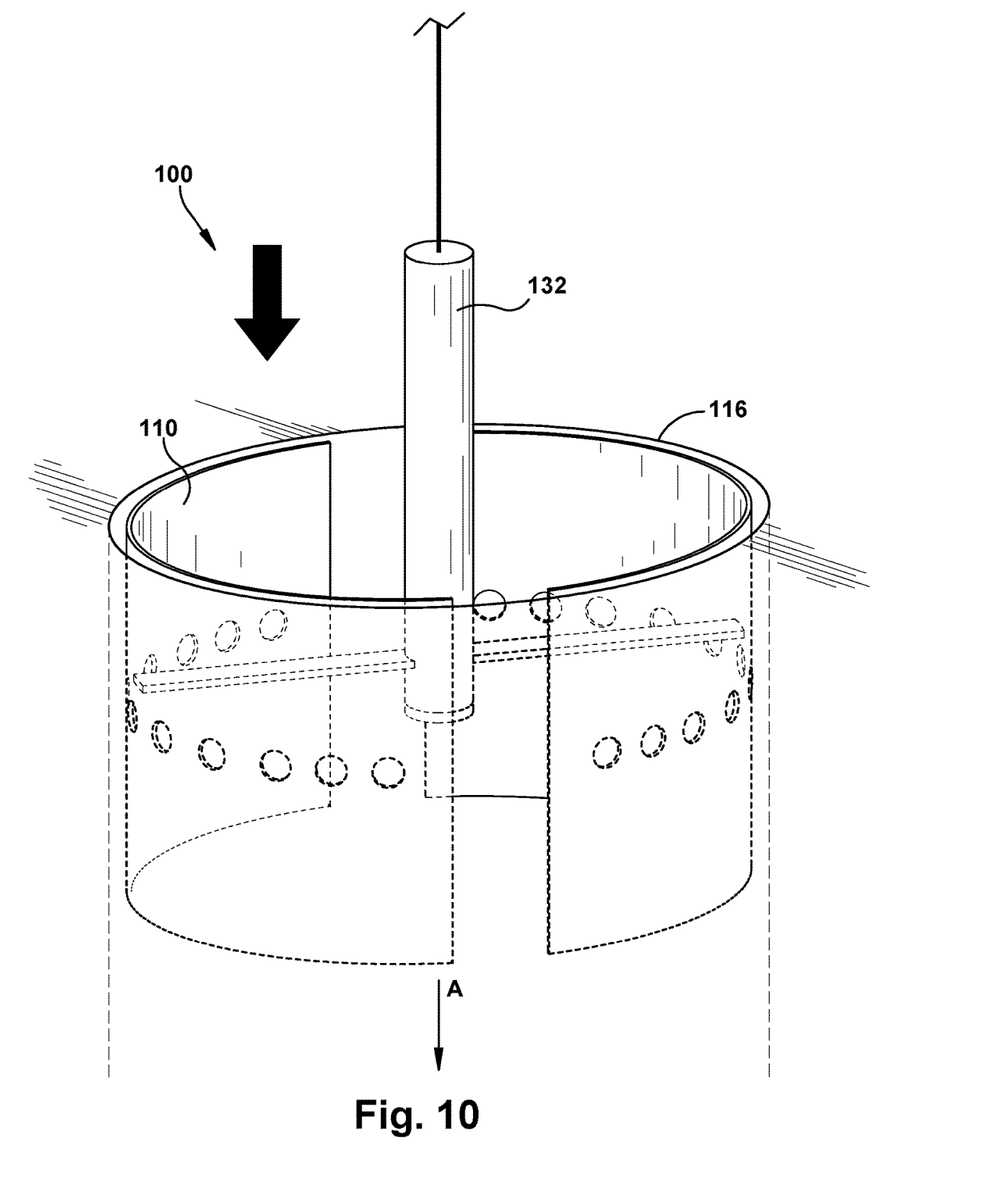

Process P2: rotating probe 100 at least ninety degrees around primary axis (A) of substantially round hole 116 after feeding probe 110 completely through substantially round hole 116 (FIG. 10). This can include rotating, by hand, tool or other holder, handle 132 until probe 100 has moved at least one-quarter turn around primary axis (A). As noted herein, this amount of rotation allows probe 100 to target the entire inner surface of substantially round hole 116 without the need to over-rotate. It is understood that probe 100 remains active during this rotation process.

Figure 11:
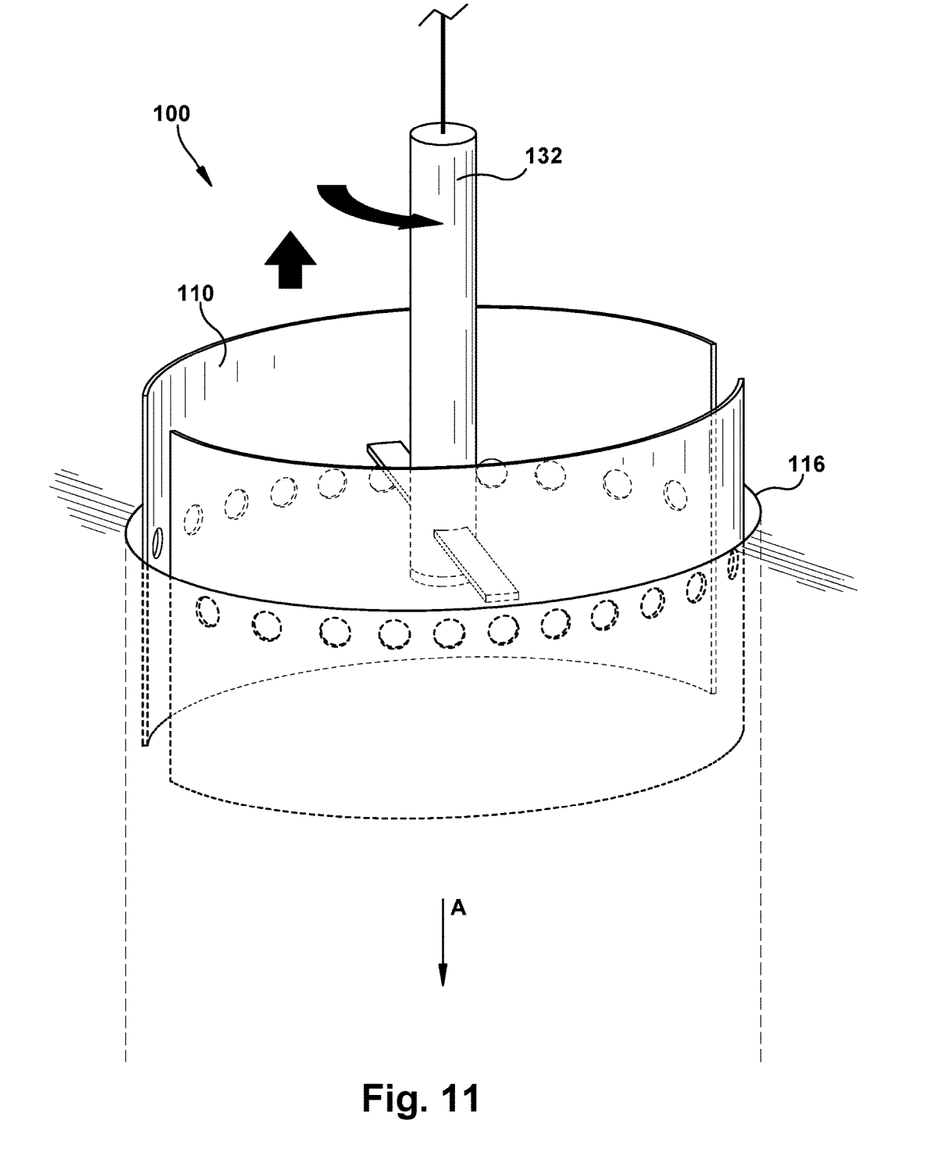
Figure 12:
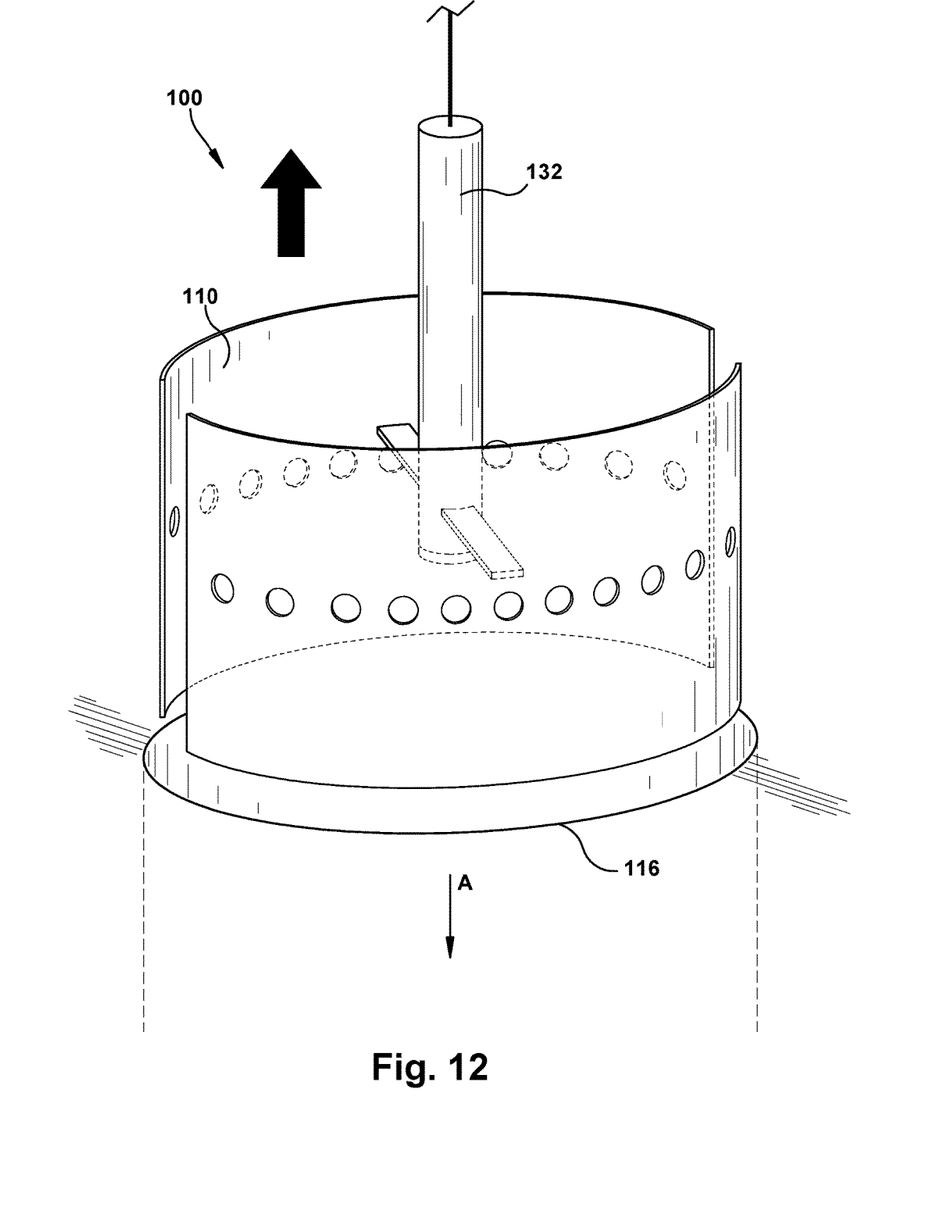

Process P3: removing probe 100 axially from substantially round hole 116 after rotating probe 110 at least ninety degrees while activated (FIG. 11). This process can include axially (along axis A) pulling or otherwise displacing probe 100 from substantially round hole 116, while keeping probe 100 active (via inspection system 102).

Process P4: compiling at least one of eddy current data or ultrasound data (at inspection system 102) about hole 116 from the feeding of probe 100 axially into substantially round hole 116 and removing of probe 100 axially from substantially round hole 116. This process can include aligning the eddy current data or ultrasound data about hole 116 from the insertion, rotation and removal processes (processes P1-P3) to develop a complete depiction of substantially round hole 116 in terms of eddy current or ultrasound response.

In some embodiments, prior to process P1, a preliminary process P0A can include calibrating probe 100 prior to feeding probe 100 axially into substantially round hole 116. That is, as shown in the schematic depiction of FIG. 12, the calibrating process can include placing probe 100 within a calibration sample 300 which replicates a shape of substantially round hole 116. In various embodiments, calibration sample 300 includes an aperture 302, or forms aperture 302, that has an approximately (+/−3%) identical size and/or shape of substantially round hole 116. Calibration sample 300 can be formed of a similar material as material 118. In some cases, calibrating probe 100 can include placing probe 100 within calibration sample 300 (shown in FIG. 12), initiating the non-destructive signal using inspection system 102, compiling eddy current data and/or ultrasound data about calibration sample 300 at inspection system 102, and adjusting the non-destructive signal in response to the eddy current data or ultrasound data deviating from an expected response (e.g., eddy current or ultrasound response, depending upon signal type(s)) for calibration sample 300. The expected response of calibration sample 300 can be stored as calibration data at inspection system 102, and can include empirical data or model-based data about eddy current and/or ultrasound responses of different materials, including the material that forms calibration sample 300.

In various embodiments, Processes P0-P4, and use of probe 100, may be particularly beneficial for inspecting bolt holes in a component. That is, in some cases, where substantially round hole 116 is a bolt hole (e.g., a hole with internally threaded walls), probe 100 may be used for inspecting that hole 116.

Figure 13:
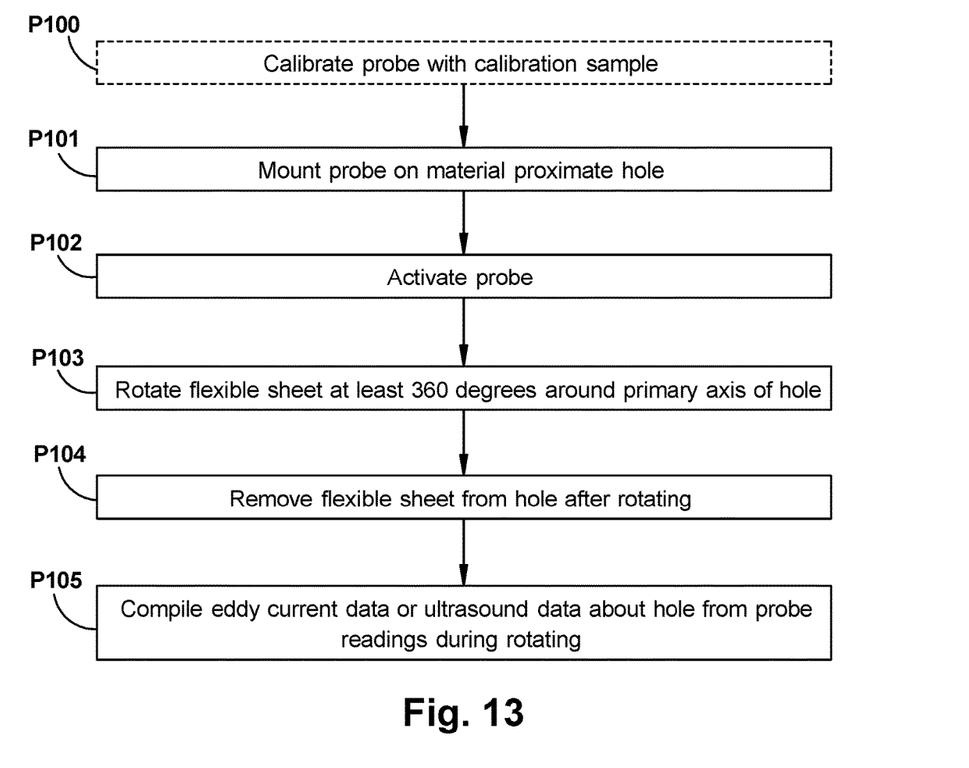
FIG. 13 shows a flow diagram illustrating processes according to various aspects of the disclosure.

FIG. 13 shows a flow diagram illustrating processes in a method according to various embodiments of the disclosure. These processes are illustrated along with the schematic depictions of probe 200 in FIGS. 4-7 and the corresponding depictions in FIGS. 14 and 15. In various embodiments, processes in the flow diagram of FIG. 13 include:

Process P101: mount probe 200 on material 118 proximate substantially round hole 116. In various embodiments, this process can include mating bearing plate 212 with end 216 of substantially round hole 116 to couple probe 200 with material 118, as described herein with respect to FIG. 4. Probe 200 can include mating surface 232, which may include flexible sheet 234.

Process P102: activate probe 200, as discussed herein, using inspection system 102 to activating probe 200, to transmit non-destructive signals (e.g., eddy current or ultrasound signals) while probe 200 is inside hole 116.

Figure 14:
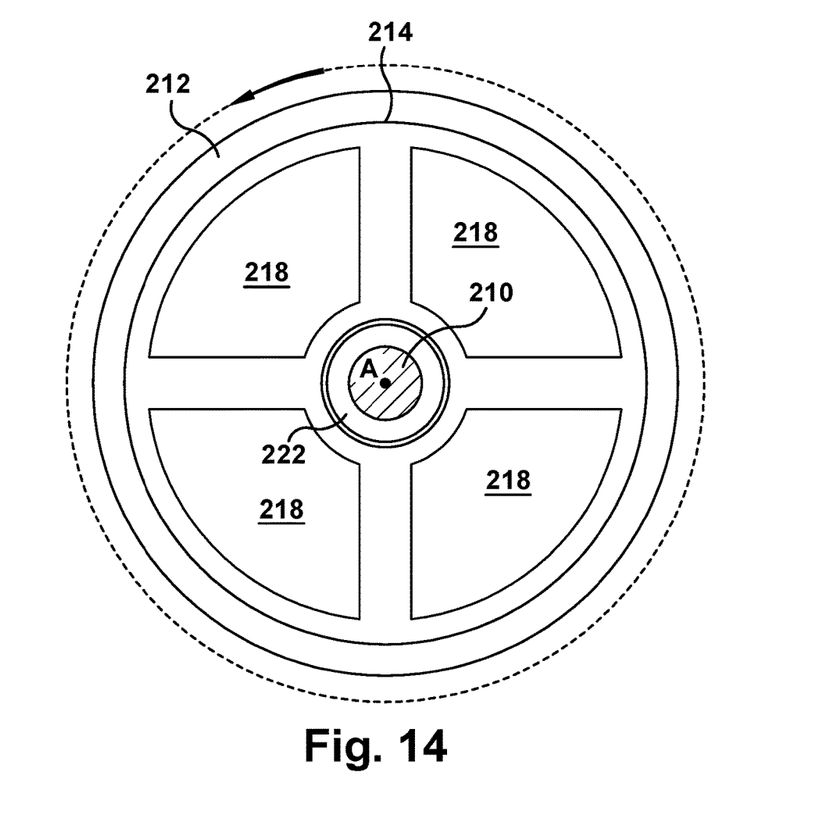
FIG. 14 shows a side view of the bearing plate of the probe of FIG. 4, performing a process according to the flow diagram of FIG. 13.
Figure 15:
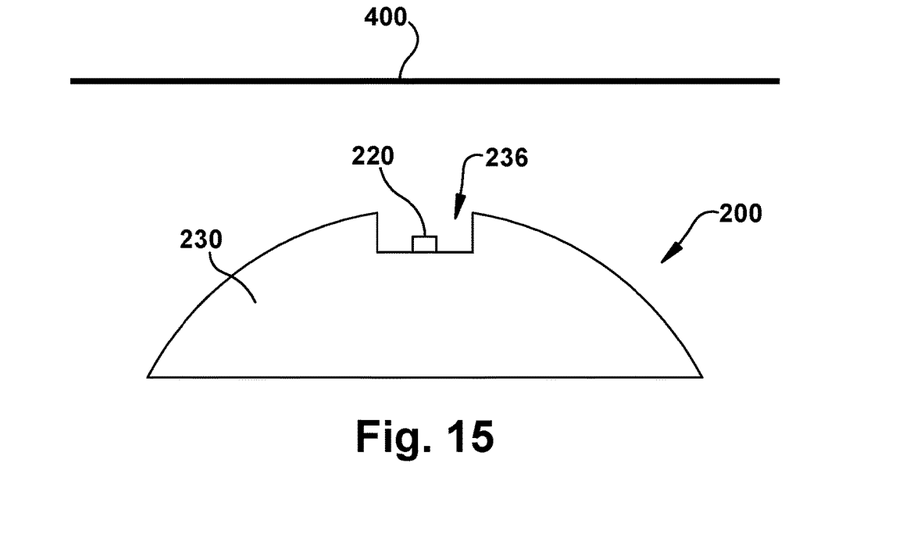
FIG. 15 shows a plan view of the sensor mount surface of the probe of FIG. 4, performing a calibration process according to the flow diagram of FIG. 13.

Process P103: rotating probe 200 at least three-hundred and sixty (360) degrees around primary axis (A) of substantially round hole 116 after activating probe 200. FIG. 14 illustrates rotation of probe (with reference to sensor support 210) around primary axis (A) of hole 116. This can include rotating, by hand, tool or other holder, sensor support 210 until probe 200 has moved at least completely around primary axis (A). As noted herein, this amount of rotation allows probe 200 to target the entire inner surface of substantially round hole 116 without the need to over-rotate. It is understood that probe 200 remains active during this rotation process. In some cases, probe 200 can be rotated approximately three-hundred and seventy (370) degrees around primary axis (A) to ensure that inspection system 102 has data about the entire inner circumference of hole 116, with minimal overlap in eddy current or ultrasound data.

Process P104: removing probe 200 axially from substantially round hole 116 after rotating probe 200 at least three-hundred and sixty degrees. This process can include axially (along axis A) pulling or otherwise displacing probe 200 from substantially round hole 116.

Process P105: compiling at least one of eddy current data or ultrasound data (at inspection system 102) about hole 116 from the rotating of probe 200 about axis A within substantially round hole 116. This process can include aligning the eddy current data or ultrasound data about hole 116 from the rotation to develop a complete depiction of substantially round hole 116 in terms of eddy current or ultrasound response. It is understood that Process P105 can be performed prior to process P104, or contemporaneously with process P104.

In some embodiments, prior to process P101, a preliminary process P100 can include calibrating probe 200 prior to mounting probe 200 proximate substantially round hole 116. That is, as shown in the schematic depiction of FIG. 15, the calibrating process can include placing probe 200 proximate a flat plate 400, which may be formed of a metal or composite material. In some cases, flat plate 400 is formed of a similar material as material 118. In some cases, calibrating probe 200 can include placing probe 200 proximate (e.g., within probing range, such as approximately one (1) millimeter to approximately several millimeters) flat plate 400 (shown in FIG. 15), initiating the non-destructive signal using inspection system 102 (FIG. 4), compiling eddy current data and/or ultrasound data about flat plate 400 at inspection system 102, and adjusting the non-destructive signal in response to the eddy current data or ultrasound data deviating from an expected response (eddy current or ultrasound response, depending upon signal type(s)) for flat plate 400. The expected response of flat plate 400 can be stored as calibration data at inspection system 102, and can include empirical data or model-based data about eddy current and/or ultrasound responses of different materials, including the material that forms flat plate 400.

In various embodiments, Processes P100-P105, and use of probe 200, may be particularly beneficial for inspecting boreholes in a component. That is, in some cases, where substantially round hole 116 is a bore (e.g., a hole without internally threaded walls), probe 200 may be used for inspecting that hole 116.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A method of inspecting a substantially round hole in a material, the method comprising:
   feeding a probe axially into the substantially round hole until the probe completely passes through the substantially round hole while the probe is activated, the probe including:
      a flexible sheet shaped and biased to substantially conform with a portion of an interior of the substantially round hole; and
      a plurality of sensors disposed on the flexible sheet, each sensor configured to transmit a non-destructive signal into the material for inspecting the substantially round hole;
   rotating the probe at least ninety degrees around a primary axis of the substantially round hole after feeding the probe completely through the substantially round hole;
   removing the probe axially from the substantially round hole after rotating the probe at least ninety degrees while the probe is activated; and
   compiling at least one of eddy current data or ultrasound data about the hole from the feeding of the probe axially into the substantially round hole and the removing of the probe axially from the substantially round hole.

2. The method of claim 1, further comprising calibrating the probe prior to feeding the probe axially into the substantially round hole.

3. The method of claim 2, wherein the calibrating includes:
   placing the probe within a calibration sample which replicates a shape of the substantially round hole;
   initiating the non-destructive signal into the calibration sample from the probe;
   compiling at least one of eddy current data or ultrasound data about the calibration sample; and
   adjusting the non-destructive signal in response to the at least one of eddy current data or ultrasound data deviating from an expected eddy current or ultrasound response for the calibration sample.

4. The method of claim 2, wherein the calibrating includes:
   placing the probe proximate a flat plate;
   initiating the non-destructive signal into the flat plate from the probe;
   compiling at least one of eddy current data or ultrasound data about the flat plate; and
   adjusting the non-destructive signal in response to the at least one of eddy current data or ultrasound data deviating from an expected eddy current or ultrasound response for the flat plate.

5. The method of claim 1, wherein the probe further includes a probe support coupled with the flexible sheet, the method further comprising:
   mounting the probe support on the material proximate the substantially round hole.

6. The method of claim 1, wherein the substantially round hole is a bolt hole or a borehole in the material.

7. The method of claim 1, wherein the non-destructive signal includes one of an eddy current signal and an ultrasound signal.

8. The method of claim 1, wherein the plurality of sensors in the probe extend along a line on the flexible sheet.

9. A method of inspecting a substantially round hole in a material, the method comprising:
   mounting a probe on the material proximate the substantially round hole, the probe including:
      a flexible sheet shaped and biased to substantially conform with a portion of an interior of the substantially round hole;
      a plurality of sensors disposed on the flexible sheet, each sensor configured to transmit a non-destructive signal into the material for inspecting the substantially round hole; and
      a probe mount coupled with the flexible sheet, the probe mount for mounting on the material;
   activating the probe;
   rotating the flexible sheet at least three-hundred-and-sixty degrees around a primary axis of the substantially round hole after inserting the flexible sheet into the substantially round hole and activating the probe;
   removing the flexible sheet from the substantially round hole; and
   compiling at least one of eddy current data or ultrasound data about the hole from the, the at least one of eddy current data or ultrasound data gathered during the rotating of the flexible sheet within the substantially round hole.

10. The method of claim 9, further comprising calibrating the probe prior to mounting the probe on the material proximate the substantially round hole.

11. The method of claim 10, wherein the calibrating includes:
   placing the probe proximate a flat plate;
   initiating the non-destructive signal into the flat plate from the probe;
   compiling at least one of eddy current data or ultrasound data about the flat plate; and
   adjusting the non-destructive signal in response to the at least one of eddy current data or ultrasound data deviating from an expected eddy current or ultrasound response for the flat plate.

12. The method of claim 9, wherein the substantially round hole includes a borehole in the material.

13. The method of claim 9, wherein the non-destructive signal includes one of an eddy current signal and an ultrasound signal.

14. The method of claim 9, wherein the plurality of sensors in the probe extend along a line on the flexible sheet.

15. The method of claim 9, wherein the rotating includes rotating the flexible sheet at least three-hundred-and-seventy degrees around the primary axis of the substantially round hole.

16. The method of claim 9, wherein mounting the probe includes inserting the probe into the substantially round hole.

* * * * *